United States Patent [19]

Szycher et al.

[11] E Patent Number: Re. 32,991

[45] Reissued Date of Patent: Jul. 18, 1989

[54] DRUG DISPENSING WOUND DRESSING

[75] Inventors: Michael Szycher, Lynnfield; Donald J. Dempsey, Newbury; Jonathan L. Rolfe, North Easton, all of Mass.

[73] Assignee: Thermedics, Inc., Woburn, Mass.

[21] Appl. No.: 223,896

[22] Filed: Jul. 25, 1988

Related U.S. Patent Documents

Reissue of:

[64] Patent No.: 4,614,787
Issued: Sep. 30, 1986
Appl. No.: 670,810
Filed: Nov. 13, 1984

[51] Int. Cl.[4] ..... C08G 18/10; C08G 18/30; A61F 13/00; A61L 1/00; A01N 25/10; B05D 3/02; B32B 7/00; C09J 7/02

[52] U.S. Cl. ..... 528/75; 522/6; 522/44; 522/46; 604/304; 604/372; 424/411; 424/78; 252/381; 252/387; 252/397; 427/2; 427/389.9; 428/254; 428/354; 512/4; 523/102

[58] Field of Search ..... 528/75; 522/6, 44, 46; 604/304, 372; 424/28, 32; 252/381, 387, 397; 427/2, 389.9; 428/254, 354; 512/4; 523/102

[56] References Cited

U.S. PATENT DOCUMENTS

| | | | |
|---|---|---|---|
| 3,062,210 | 11/1962 | Scholl | 128/156 |
| 3,342,183 | 9/1967 | Edenbaum | 128/268 |
| 3,374,134 | 3/1968 | Waldman | 156/239 |
| 3,526,224 | 9/1970 | Potts | 128/156 |
| 3,567,119 | 3/1971 | Wilbert et al. | 239/6 |
| 3,570,482 | 3/1971 | Emoto et al. | 128/156 |
| 3,598,122 | 8/1971 | Zaffaroni | 128/268 |
| 3,598,123 | 8/1971 | Zaffaroni | 128/268 |
| 3,731,683 | 5/1973 | Zaffaroni | 128/268 |
| 3,742,951 | 7/1973 | Zaffaroni | 128/268 |
| 3,842,832 | 10/1974 | Wideman et al. | 128/169 |
| 3,870,593 | 3/1975 | Elton et al. | 161/159 |
| 3,975,567 | 8/1976 | Lock | 428/315 |
| 4,034,751 | 7/1977 | Hung | 128/156 |
| 4,038,239 | 7/1977 | Coyner et al. | 528/75 |
| 4,144,317 | 3/1979 | Higuchi et al. | 424/21 |
| 4,156,067 | 5/1979 | Gould | 528/73 |
| 4,189,467 | 2/1980 | von Bittera et al. | 424/14 |
| 4,209,605 | 6/1980 | Hoy et al. | 528/54 |
| 4,215,684 | 8/1980 | Westip | 128/156 |
| 4,236,550 | 12/1980 | Braun et al. | 139/421 |
| 4,306,551 | 12/1981 | Hymes et al. | 128/156 |
| 4,307,717 | 12/1981 | Hymes et al. | 128/156 |
| 4,321,117 | 3/1982 | Kaetsu et al. | 521/28 |
| 4,331,135 | 5/1982 | Westip | 128/156 |
| 4,336,243 | 6/1982 | Sanvordeker | 424/28 |
| 4,340,043 | 7/1982 | Seymour | 128/132 |
| 4,391,106 | 7/1983 | Schafer et al. | 66/193 |
| 4,411,754 | 10/1983 | Kaetsu et al. | 424/78 |
| 4,447,590 | 3/1984 | Szycher | 528/76 |
| 4,460,369 | 7/1984 | Seymour | 604/897 |
| 4,476,697 | 10/1984 | Schafer et al. | 66/193 |
| 4,483,759 | 11/1984 | Szycher et al. | 522/20 |
| 4,496,535 | 1/1985 | Gould et al. | 424/19 |

FOREIGN PATENT DOCUMENTS

| | | |
|---|---|---|
| 273966 | of 0000 | Australia . |
| 3239318A1 | 5/1983 | Fed. Rep. of Germany . |
| 2017113A | 3/1979 | United Kingdom . |
| 2123012A | 5/1983 | United Kingdom . |

*Primary Examiner*—John Kight
*Assistant Examiner*—Nathan M. Nutter
*Attorney, Agent, or Firm*—Lorusso & Loud

[57] ABSTRACT

The disclosed wound dressings have a drug dispersed throughout a polyurethane matrix that is the reaction product of: (A) An isocyante terminated prepolymer formed by reaction of isophorone diisocyanate and a marcoglycol and (B) a monomer containing hydroxyl and vinyl groups. The reaction product is a vinyl terminated polyurethane oligomer which is liquid at room temperature and which may be readily admixed with a pharmacoactive substance and a photosensitizer, formed into a film and cured by exposure to UV light without release of heat.

In the most preferred embodiments the foregoing oligomer is codissolved in an organic solvent with a polyurethane polymer which is the reaction product of:

dicyclohexyl methane diisocyanate;

a polytetramethylene ether polyol having a molecular weight in the range of 1000–3000 daltons; and 1,4-butane diol.

That solution is then admixed with the pharmacoactive agent, formed into a film and cured.

68 Claims, No Drawings

DRUG DISPENSING WOUND DRESSING

Matter enclosed in heavy brackets [ ] appears in the original patent but forms no part of this reissue specification; matter printed in italics indicates the additions made by reissue.

BACKGROUND OF THE INVENTION

There has long been a need for a wound dressing which is soft, pliable and elastic, yet high in tensile strength and abrasion resistance and which can release drugs at a controlled, sustained level.

Presently available bandages made of materials such as cotton are undesirable because they retain water, serve as growth mediums for bacteria, and soak up tissue pieces and blood which clots, causing adhesion to the wound and trauma during removal.

Other bandages are made with plastic coverings with an adhesion coating to decrease the undesirable water absorption of cotton wound dressings. Unfortunately, new problems were created due to lack of oxygen transmission through the plastic coating. Indeed, holes had to be punched through the plastic covering to allow the transmission of some oxygen to the skin below. Hard plastic or silicone coatings were also applied to the side of the bandage adjacent to the wound to prevent adhesion. These coatings did not significantly decrease the problem of the bandage sticking to the wound, and blocked oxygen and water transmission.

In further attempts to overcome the adhesion and permeability problems, polyurethane and other plastic dressings were tried. For example, U.S. Pat. No. 3,975,567 to Lock discloses a pressure and heat-treated polyurethane foam which is lyophilic.

Other polyurethanes which polymerize upon exposure to ultraviolet light were also developed. The majority of these UV-curable polyurethanes were designed for use as orthopedic casts, e.g., U.S. Pat. No. 4,209,605. Other types of polymers have been used as matrices for incorporation of biologically active agents and, in the form of polymerized sheets or films, have been used as wound dressings, such as the compounds disclosed by U.S. Pat. Nos. 4,321,117 (acrylic polymers) and 4,156,067 (polyurethane). None of these compositions managed to combine the properties of softness, oxygen and water vapor permeability, flexibility, thixotropy and capability for incorporation of biologically active agents, with a fast cure at room temperature to a tough, colorless film. The ability to cure at room temperature without release of heat is particularly important because many drugs are heat labile.

At present, the most commercially successful burn and superficial skin wound dressing is a polyether-based polyurethane, moisture-vapor permeable membrane compounded with silica gel. The composition, known as "Op-Site"®, described in U.S. Pat. Nos. 4,340,043 and 4,460,369 assigned to Smith & Nephew Research Ltd., is in the form of a thin film having a surface coated with a polyvinylethylether adhesive. Although considerably more comfortable, permeable, and effective as protection against bacterial contamination than the prior art wound dressings, this material still suffers from the inability to incorporate biologically active agents such as coagulants and antibiotics into the membrane, rather than into the adhesive, and from difficulty in formation and application as a bandage which conforms to the contour of the site of application. In connection with this latter problem, two to three people are required for application.

It is therefore an object of the present invention to provide a wound dressing which physically incorporates drugs such as antibiotics, coagulants, and anti-inflammatories into the dressing structure having appreciable tensile strength rather than into the adhesive or thin coating on the dressing so that the drugs are released in a controlled, sustained manner.

It is a further object of the present invention to provide a material for use as a wound dressing which is strong yet flexible, and which can be made to conform to the shape of the site of the wound.

It is a still further object of the present invention to provide such a material for use as a wound dressing which is nontoxic, non-carcinogenic, and biocompatible.

It is a further object of the present invention to provide a material which can be easily formed and applied to a wound by one person in adverse circumstances.

Yet a further object of the invention is to provide a polymeric material which is a liquid at room temperature and which has a sufficiently low viscosity at room temperature (prior to cure) to facilitate admixture with a drug to form a homogeneous blend.

Still a further object is to provide such a polymeric material which cures at room temperature without release of heat (non-exothermic).

The foregoing and other objects and features of the claimed invention will be understood by those skilled in the art from a reading of the description which follows.

SUMMARY OF THE INVENTION

A polyurethane has now been discovered which is compatible with a wide range of pharmacoactive agents and which, in the form of an oligomer (uncured) which is a liquid at room temperature, may be admixed in liquid state with one or more pharmacoactive agents. Because the cure is not exothermic to any appreciable degree, curing may be conducted without cooling and with no increase in temperature. The cured polyurethane elastomer is crystal clear, soft and elastomeric. Applied to a wound in the form of a film, the polyurethane serves to release the incorporated drug at a controlled, sustained rate while protecting that portion of the incorporated drug yet to be released. The polyurethane product is hydrophilic in nature and solvent resistant.

More specifically, the wound dressings of the present invention have a drug dispersed throughout a polyurethane matrix that is the reaction product of:

A. an isocyanate terminated prepolymer formed by reaction of isophorone diisocyanate and a macroglycol; and B. a monomer containing hydroxyl and vinyl groups. This reaction product is a vinyl terminated polyurethane oligomer which is liquid at room temperature. This liquid oligomer may be readily admixed with a pharmacoactive substance and a photosensitizer, formed into a film and curved by exposure to UV light without release of heat.

In the most preferred embodiments the foregoing oligomer is codissolved in an organic solvent with a polyurethane polymer which is the reaction product of: dicyclohexyl methane diisocyanate; a polytetramethylene ether polyol having a molecular weight in the range of 1000–3000; Daltons and 1,4-butane diol. The pharmacoactive agent and photoinitiator are then admixed into the solution and a film is formed and cured.

DESCRIPTION OF THE PREFERRED EMBODIMENTS

At the outset, the invention is described in its broadest overall aspects with a more detailed description following.

The drug dispensing composition of the present invention is formed by reacting isophorone diisocyanate and a macroglycol together to form an isocyanate terminated prepolymer and then reacting the prepolymer with a chain terminator to form a vinyl terminated polyurethane oligomer. The drug and, optionally, a photoinitiator may be admixed with the foregoing compounds at any point prior to curing to form a homogeneous admixture. The homogeneous admixture is formed into a liquid film and cured to form the wound dressing with one side of the cured film optionally provided with a pressure sensitive adhesive.

The isophorone diisocyanate (IPDI) used in the present invention is an aliphatic compound having the following formula:

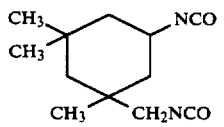

IPDI is utilized in the present invention because it is a liquid at room temperature, because it cures to a crystal clear product upon exposure to ultraviolet light, rather than yellowing as is the case with many prior art diisocyanates, and because it cures without any temperature rise.

The macroglycol preferred for use in the present invention is a polypropylene glycol (PPG), preferably having a molecular weight of 500–5000 daltons and, more preferably 1000–3000 daltons. PPG is preferred because it reacts with the IPDI at a fast rate at room temperature with no temperature rise. Other high molecular weight glycols such as polyethylene glycol (PEG) may be employed, but PEG is a solid at room temperature and a feasible rate of reaction would require heating. As used herein, the term "macroglycol" has reference to any glycol having a molecular weight in excess of 500 daltons.

The chain terminator used in formulating the products of the invention should have both hydroxyl and vinyl functional groups and is preferably an acrylic compound such as hydroxyethyl acrylate or hydroxyethyl methacrylate. Hydroxyethyl methacrylate (HEMA) is most preferred for use as the chain terminator.

A large variety of drugs, including heat labile drugs, may be incorporated into the compositions of the present invention at any point within the formulation/reaction sequence because the process of the present invention does not involve any exothermic reaction and, therefore, no cooling of any reaction mixture is required prior to the addition of a drug having activity highly susceptible to degradation by heat. However, it is preferred that the drug be added to the uncured liquid, vinyl-terminated oligomer as the last additive prior to curing and after aeration for removal of all entrained gases. It is contemplated that any coagulant, antibiotic, antifungal agent, topical anesthetic, anti-inflammatory agent or mixture thereof might be incorporated into any one of the liquid precursors of the cured product. In the examples which follow thrombin is mentioned as a coagulant and gentamycin sulfate is mentioned as a wide-spectrum antibiotic but those specifically mentioned drugs are merely exemplary of the wide range of drugs that would be useful here.

Photosensitizers useful herein include benzophenone, acteophenone, azobenzene, acenaphthenequinone, o-methoxy benzophenone, thioxanthen-9-one, xanthen-9-one, 7-H-Benz(de) anthracen-7-one, 1-naphthaldehyde 4,4'-bis(dimethylamino)benzophenone, fluorene-9-one, 1'-acetonaphthone, 2'-acetonaphthone, anthraquinone, 2-tert.-butyl anthraquinone, 4-morpholinobenzophenone, p-diacetylbenzene, 4-aminobenzophenone, 4'-methoxyacetophenone, diethoxyacetophenone, benzaldehyde, and the like.

Specifically useful herein are acetophenone photosensitizers of the structure:

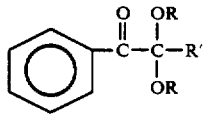

wherein R is alkyl of from 1 to about 8 carbon atoms, or aryl of 6 ring carbon atoms and R' is hydrogen, alkyl of from 2 to about 8 carbon atoms, aryl of from 6 to 14 carbon atoms, or cyclo alkyl of 5 to 8 ring carbon atoms.

Diethoxyacetophenone is the preferred photosensitizer.

The diisocyanate, macroglycol and chain terminator are reacted in approximately stoichiometric amounts, i.e., in the approximate ratio of 2 moles (2.0 equiv.) isophorone diisocyanate to 1 mole (1.0 equiv.) macroglycol to 2 moles (1.0 equiv.) chain terminator. At the end of the reaction between the prepolymer and the chain terminator free isocyanate is monitored by infrared spectrophotometry and, if necessary, additional small amounts of the chain terminator may be added to scavenge any remaining isocyanate. It is important that the low molecular weight monomers present in the composition be reacted prior to contact with the skin so that only compounds with molecular weights of 1500–5000 Daltons are present. The high molecular weight compounds do not leach out of the wound dressing into the underlying tissue and are therefore non-toxic.

An antioxidant such as tetrakis [methylene (3,5-di-tert-butyl-4-hydroxyhydrocinnamate)] may be added to inhibit spontaneous oxygen-initiated curing. A polyurethane catalyst such as dioctyl tin dilaurate, N-methyl morpholine, trimethylamine, triethylamine, zinc octoate, and dibutyl tin dilaurate is added to both the reaction medium in which the prepolymer is formed and the reaction medium in which the prepolymer is reacted with the chain terminator.

The performed wound dressings require a material which exhibits thixotropic behavior: a very high apparent viscosity which decreases rapidly under shear stress. Thixotropic behavior is necessary to allow the uncured wound dressings to conform to body geometry, and to prevent sagging when the dressing is applied to vertical surfaces. Thixotropic behavior may be induced by varying the molecular weight of the macroglycol (the higher the molecular weight, the thicker the uncured dressing); by adding a non-reactive thixotropic agent; or by a combination of the two methods. The tensile strength and hardness of the polyurethane is also varied by varying the molecular weight of the PPG. As the molecular weight is decreased, the tensile strength and hardness are increased. As the molecular weight is in creased, the tensile strength and hardness are decreased.

Nonreactive thixotropic agents include pyrogenic silica such as Cab-O-Sil M-5® and Cab-O-Sil N70TS® from the Cabot Company and bentonitte clays. Generally speaking, addition of 1.0 part Cab-O-Sil M-5® to 100 parts urethane oligomer increases the apparent viscosity by a factor of 10,000.

To produce a thixotropic or shear-sensitive, high viscosity liquid, ultraviolet radiation curable oligomer, the vinyl terminated oligomer is dissolved together with TECOFLEX®EG-60D in an organic solvent. Preferably, 80–99 parts by wt. of the vinyl-terminated oligomer are used per 1–20 parts by wt of said polyurethane polymer. The resulting solution is thixotropically thickened by the addition of high surface area fumed silica particles. The preferred thixotropic composition is formed from 88 grams of the oligomer of Example 3 dissolved with 12 grams TECOFLEX®EG-60D in 2000 grams methylene chloride, 10 grams of fumed silica Cab-O-sil M-5® is added. The resulting thixotropic mixture is suitable for the production of continuous liquid films and displays a viscosity of 370 cps at 23° C. at 20 RPM on spindle #2.

TECOFLEX® the tradename of Thermedics Inc. for a polyurethane which is the reaction product of (1) dicyclohexyl methane diisocyanate, (2) a polytetramethylene ether polyol having a molecular weight in the range 1000–3000 Daltons and (3) 1,4-butane diol and is further described in U.S. patent application Ser. No. 600,568 filed Apr. 17, 1984 in the name of Michael Szycher, the teachings of which are incorporated herein by reference.

The presence of a thixotropic agent and the increased viscosity does not affect cure rate since the silica particles are transparent to UV radiation.

A film of the resulting mixture can be formed by drawing, rolling, or spraying using techniques well known in the art. Optionally, the film may be formed on a textile fabric. Curing may be accomplished by exposure to ultraviolet radiation, typically between 219 and 425 nm for 20 seconds at 0.5 $W/cm^2$. Curing transforms the liquid oligomer into a solid elastomer.

The cured polyurethane product is crystal clear, soft and elastomeric and serves to release the incorporated drug at a controlled, sustained rate while protecting that portion of the incorporated drug yet to be released. The product is hydrophilic in nature and solvent resistant.

Any pressure-sensitive adhesive conventionally used for wound dressings or bandages may be spread over one surface of the cured film, e.g. a polyacrytate adhesive or a polyvinylethyl ether blend adhesive. A release paper or plastic film is then applied over the exposed surface of the adhesive.

The examples which follow serve to further illustrate the present invention but should not be considered as limiting; rather, the scope of the invention is defined by the claims which follow.

EXAMPLE 1

A four liter reactor equipped with continuous nitrogen blanketing and a heating mantel is charged with 81.6 grams isophorone diisocyanate, 245.2 g of 2,000 molecular weight polypropylene glycol and 0.1% by weight dioctyl tin dilaurate.

Agitation is begun and the mixture is raised to and maintained at 60° C. After three hours, 64 grams hydroxyethyl methacrylate (HEMA) is added with an additional 0.1% by weight dioctyltin dilurate.

The mixture is allowed to react exothermally to 110° C. for two hours.

At the end of this reaction, free isocyanate is monitored by infrared spectrophotometry, and if necessary small amounts of hydroxyethyl methacrylate may then be added (up to 2 gm) to scavenge any remaining isocyanate.

0.1% by weight of IRGANOX 1010*, and 4% by weight diethoxy acetophenone (DEAP, a photoinitiator) is then added and the mixture agitated and deaerated.

*tradename of Ciba Geigy for tetrakis [methylene (3,5-di-tert-butyl-4-hydroxy-hydrocinnamate)], an antioxidant.

A film of the resulting mixture can be formed by drawing, rolling, or spraying by techniques well known in the art.

Curing may be accomplished by exposure to ultraviolet radiation, typically between 219 and 380 nanometers for 20 seconds at 0.5 watts per square centimeter.

This results in a fully cured, solvent-resistant hydrophilic transparent elastomer with the following physical properties: tensile strength 600 P.S.I., elongation 150%, hardness (shore A) 55.

EXAMPLE 2

A four liter reactor equipped with continuous nitrogen blanketing and a heating mantel is charged with 102 grams IPDI, 229.2 grams 1,000 molecular weight polypropylene glycol, and 0.1% by weight dioctyltin dilaurate.

Agitation is begun and the mixture is raised to and maintained at 60° C. After three hours, 59.60 grams of HEMA is added with an additional 0.1% by weight dioctyltin dilaurate.

The mixtrue is allowed to react exothermally to 110° C. for two hours.

At the end of this reaction, free isocyanate is monitored by infrared spectrophotometry, and if necessary small amounts of HEMA are added to to scavenge any remaining isocyanate.

0.1% by weight of IRGANOX 1010® and 4% by weight diethoxy acetophenone are then added and the mixture agitated and deaerated.

A film of the resulting mixture can be formed by drawing, rolling, or spraying by techniques well known in the art.

Curing may be accomplished by exposure to ultraviolet radiation, typically between 219 and 380 nanometers for 20 seconds at 0.5 watts per square centimeter.

This results in a fully cured, solvent-resistant, hydrophilic, transparent elastomer with the following physical properties: tensile strength: 950 PSI, elongation 150%, hardness, (shore A) 55.

EXAMPLE 3

A four liter reactor equipped with continuous nitrogen blanketing and a heating mantel is charged with 101.6 grams IPDI, 228.8 grams 1,000 molecular weight polypropylene glycol and 0.1% by weight dioctyl tin dilaurate.

Agitation is begun and the mixture is raised to and maintained at 60° C. for two hours. Thereafter, 55.3 g HEMA is added with an additional 0.1% by weight dioctyltin dilaurate.

At the end of this reaction, free isocyanate is monitored by infrared spectrophotometry, and if necessary small additions of hydroxyethyl methacrylate may then be made (up to 2 gm) to scavenge any remaining isocyanate. The result is the preferred oligomer.

0.1% by weight of IRGANOX 1010® and 4% by weight diethoxyacetophenone are then added and the mixture agitated and deaerated.

A film of the resulting mixture can be formed by drawing, rolling, or spraying by techniques well known in the art.

Curing may be accomplished by exposure to ultraviolet radiation, typically between 219 and 380 nanometers for 20 seconds at 0.5 watts per square centimeter.

This results in a fully cured, solvent-resistant, hydrophilic, transparent elastomer with the following physical properties: tensile strength: 950 PSI, elongation 32.5%, hardness (shore A) 60.

EXAMPLE 4

To produce a thixotropic (shear-sensitive high viscosity liquid), UV Curable Oligomer, the preferred oligomer obtained in Example 3 is co-dissolved with TECOFLEX®EG-60D (the 65 Shore D product mentioned at p. 7 in aforementioned U.S. Ser. No. 600,568) in methylene chloride. The resulting solution is further stabilized by the addition of high surface area fumed silica particles as described below.

A preparation containing 94 grams of the oligomer from Example 2 is co-dissolved with 6 grams of TECOFLEX EG-60D® in 2000 grams of methylene chloride. To this solution, 10 grams of fumed silica (CAB-O-Sil N70TS® are added. The result is a thixotropic mixture, but it did not have sufficient viscosity to produce continuous liquid films.

EXAMPLE 5

A preparation containing 88 grams of the oligomer from example 3, admixed with the 0.1 wt. % IRGANOX® and 4 wt. % diethoxyacetophenone, is co-dissolved with 12 grams of TECOFLEX EG-60D® in 2000 grams of methylene chloride. To this solution, 10 grams of fumed silica (CAB-O-SIL M-S® are added). The result is a thixotropic mixture, suitable for the production of continuous liquid films. This mixture displays a viscosity of 370 cps at 23° C. 20 RPM, spindle #2, which is ideal for admixture with drugs to form the wound dressings of the present invention, and is the preferred thixotropic UV curable mixture.

EXAMPLE 6

The constituents of example 5 are intimately mixed for 10 minutes, and deaerated until all entrained gases are removed.

At this stage pharmacoactive substances such as 1% by weight thrombin (a coagulant) and 4% by weight gentamycin sulfate, (a wide-spectrum antibiotic) are incorporated into the above liquid by gentle mixing for 30 minutes until a uniform (homogeneous) blend is obtained.

A film of the resulting mixture is then formed by drawing, rolling, or spraying as in example 1.

Curing is accomplished by exposure to U.V. radiation, typically between 219 to 425 nanometers for 20 seconds at 0.5 watts/CM$^2$.

EXAMPLE 7

The constituents of example 5 are intimately mixed for 10 minutes, and deaerated until all entrained gases are removed.

At this stage, pharmacoactive substances such as 1% by weight thrombin (a coagulant) and 6% by weight gentamycin sulfur (a wide spectrum antibiotic), are incorporated into the above liquid by gentle mixing for 30 minutes until a uniform blend is obtained.

This example produced the preferred medicated UV-curable composition. A film of the resulting mixture may then be formed by drawing, rolling, or spraying as in example 1.

Curing is accomplished by exposure to U.V. radiation, typically between 219 to 425 nanometers for 20 seconds at 0.5 watts/CM$^2$.

EXAMPLE 8

Preparation of Medicated Wound Dressings:

Supporting fabric is saturated with TECOFLEX®SG-93A (the 95 Shore A product mentioned at p.7 of U.S. Ser. No. 600,568) hydrophobic polymer, by drawing the fabric vertically into a 12% solids solution of the hydrophobic polymer in chloroform. Pull speed is fully controlled so that a continuous film enveloping the fabric is formed, having a desired thickness of 2–4 mils.

The resulting saturated fabric is coated on one side by rolling or spraying with nitrogen the hydrophilic, thixotropic, UV-curable oligomer of Example 5, and subsequently curing the liquid into an elastomeric film by exposing the oligomer to UV radiation between 219 and 425 nm for 20 seconds at 0.5 watts/CM$^2$.

Finally, a thin coat of pressure sensitive adhesive is applied onto the cured, hydrophilic elastomeric film. The resulting multi-layered structure is then assembled on release paper, cut and packaged, and is ready to use.

The invention may be embodied in other specific forms without departing from the spirit of essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A wound dressing comprising a drug-dispensing elastomeric film, said film comprising:
   A. A cured reaction product consiting essentially of:
      (1) isophorone diisocyanate;
      (2) a macroglycol; and
      (3) a monomer containing hydroxyl and vinyl groups; and
   B. a pharmacoactive agent dispersed through said cured reaction product.

2. The cured wound dressing of claim 1 wherein the repeating molecular units of said film are cross-linked through terminal vinyl groups.

3. The wound dressing of claim 1 wherein said film has been cured by incorporation of a photosensitizer and exposure to ultraviolet light.

4. The wound dressing of claim 1 wherein said reaction product is formed by:

(a) reacting said isophorone diisocyanate and said macroglycol together in the presence of a catalyst to form an isocyanate terminated prepolymer;

(b) reacting said prepolymer with said monomer containing hydroxyl and vinyl groups to form an ultraviolet-curable, vinyl terminated polyurethane oligomer;

(c) admixing said oligomer with the pharmacoactive agent to form an UV-curable homogeneous blend;

(d) forming the UV-curable homogeneous mixture into a film; and (e) curing said film by exposure to ultraviolet light.

5. The wound dressing of claim 4 wherein said macroglycol is polypropylene glycol having a number average molecular weight of 500–5000 daltons and said monomer is hydroxyethyl methacrylate.

6. The wound dressing of claim 4 wherein said film contains 1–10 wt. % of said drug, based on the weight of said oligomer.

7. The wound dressing of claim 4 wherein said drug is selected from the group consisted of coagulants, antibiotics, antifungals, topical anesthetics, anti-inflammatories mixtures thereof.

8. The wound dressing of claim 4 further comprising a coating of a pressure sensitive adhesive on one surface of said film.

9. The wound dressing of claim 4 wherein a photoinitiator is admixed with said oligomer.

10. The wound dressing of claim 9 wherein said photoinitiator is selected from the group consisting of diacetoxyacetobenzophenone, benzophenone, diethoxyacetophenone 4-morpholine benzophenone, 4-aminobenzophenone and 4'-methoxyacetophenone.

11. The wound dressing of claim 4 wherin said film further comprises at least one non-reactive thixotropic agent.

12. The wound dressing of claim 11 wherein said non-reactive thixotropic agent is selected from the group consisting of pyrogenic silica and bentonite clays.

13. The wound dressing of claim 4 wherein the vinyl terminated oligomer is co-dissolved with a polyurethane polymer which is the reaction product of:

(d) dicyclohexyl methane diisocyanate;

(e) a polytetramethylene ether polyol having a number average molecular weight in the range of 1000–3000 Daltons; and (f) 1,4-butane diol;

and the resulting solution is formed into said film.

14. The wound dressing of claim 13 wherein said film contains 80–99 parts by weight of said vinyl terminated oligomer and 1–20 parts by weight of said polyurethane polymer.

15. The wound dressing of claim 13 further comprising a textile fabric, said film being formed on said textile fabric.

16. The wound dressing of claim 15 wherein said textile fabric is first coated with a polyurethane polymer that is the reaction product of:

dicyclohexyl methane diisocyanate;

a polytetramethylene ether polyol having a number average molecular weight in the range of 1000–3000 Daltons; and 1,4-butane diol and then coated with said solvent solution.

17. The wound dressing of claim 16 further comprising a coating of a pressure sensitive adhesive on one surface of said film.

18. The wound dressing of claim 13 wherin said film further comprises at least one non-reactive thixotropic agent.

19. The wound dressing of claim 18 wherein said non-reactive thixotropic agent is selected from the group consisting of pyrogenic silica and bentonite clays.

20. A process for forming a drug-dispensing wound dressing comprising:

(1) preparing a reaction product consisting essentially of isophorone diisocyanate, a macroglycol and a monomer containing hydroxyl and vinyl groups by reacting (a) isophorone diisocyanate and (b) a macroglycol in the presence of a catalyst to form an isocyanate terminated prepolymer and reacting said prepolymer with (c) a monomer containing hydroxyl and vinyl groups to form an ultraviolet-curable, vinyl terminated polyurethane liquid oligomer;

(2) admixing said vinyl terminated oligomer with a drug to form an UV-curable mixture;

(3) forming the UV-curable mixture into a film; and (4) curing said film by exposure to ultraviolet light.

21. The process of claim 20 wherein a photoinitiator is admixed with said oligomer and wherein said curing is at approximately room temperature.

22. The process of claim 20 wherein said macroglycol is polypropylene glycol having a number average molecular weight of 500–5000 daltons and said monomer is hydroxyethyl methacrylate.

23. The process of claim 20 wherein said drug is added in an amount 1–10% by weight, based on the weight of said oligomer.

24. The process of claim 20 wherein said drug is selected from the group consisting of coagulants, antibiotics, antifungals, topical anesthetics, amti-inflammatories and mixtures thereof.

25. The process of claim 20 further comprising coating one surface of said film with a pressure sensitive adhesive.

26. The process of claim 21 wherein said photoinitiator is selected from the group consisting of diacetoxyacetobenzophenone, benzophenone, diethoxyacetophenone, 4-morpholine benzophenone, 4-aminobenzophenone and 4'-methoxyacetophenone.

27. The process of claim 21 further comprising mixing said oligomer with at least one non-reactive thixotropic agent.

28. The process of claim 27 wherein said non-reactive thixotropic agent is selected from the group consisting of pyrogenic silica and bentonite clays.

29. A process in accordance with claim 20 wherein said vinyl terminated oligomer is dissolved in an organic solvent and the drug is admixed in said solvent solution.

30. A process in accordance with claim 29 wherein the vinyl terminated oligomer is co-dissolved with a polyurethane polymer which is the reaction product of:

(d) dicyclohexyl methane diisocyanate;

(e) a polytetramethylene ether polyol having a number average molecular weight in the range of 1000–3000 daltons; and (f) 1,4-butane diol.

31. The process of claim 30 wherein 80–99 parts by weight of said vinyl terminated oligomer are codissolved with 1–20 parts by weight of said polyurethane polymer.

32. The process of claim 30 wherein said monomer is hydroxyethyl methacrylate and said macroglycol is a polypropylene glycol having a number average molecular weight of 500–3000 daltons.

33. The process of claim 30 further comprising providing a textile fabric and coating said textile fabric with said solvent solution to form said film.

34. The process of claim 33 wherin said textile fabric is first coated with a polyurethane polymer that is the reaction product of:

dicyclohexyl methane diisocyanate;

a polytetramethylene ether polyol having a number average molecular weight in the range of 1000–3000 daltons; and 1,4-butane diol and then coated with said solvent solution.

35. A process in accordance with claim 20 wherein a sufficient amount of (c) is added so that only compounds with number average molecular weights of 1500–5000 are present.

*36. A dispensing elastomeric film, said film comprising:*

*A. A cured reaction product consisting essentially of:*

*(1) isophorone diisocyanate;*

*(2) a macroglycol; and*

*(3) a monomer containing hydroxyl and vinyl groups; and*

*B. an agent to be dispensed through said cured reaction product.*

*37. The cured dispensing elastomeric film of claim 36 wherein the repeating molecular units of said film are cross-linked through terminal vinyl groups.*

*38. The dispensing elastomeric film of claim 36 wherein said film has been cured by incorporation of a photosensitizer and exposure to ultraviolet light.*

*39. The dispensing elastomeric film of claim 36 wherein said reaction product is formed by:*

*(a) reacting said isophorone diisocyanate and said macroglycol together in the presence of a catalyst to form an isocyanate terminated prepolymer;*

*(b) reacting said prepolymer with said monomer containing hydroxyl and vinyl groups to form an ultraviolet-curable, vinyl terminated polyurethane oligomer;*

*(c) admixing said oligomer with the agent to be dispensed to form an UV-curable homogeneous blend;*

*(d) forming the UV-curable homogeneous mixture into a film; and*

*(e) curing said film by exposure to ultraviolet light.*

*40. The dispensing elastomeric film of claim 39 wherein said macroglycol is polypropylene glycol having a number average molecular weight of 500–5000 daltons and said monomer is hydroxyethyl methacrylate.*

*41. The dispensing elastomeric film of claim 39 wherein said film containing 1–10 wt. % of said agent to be dispensed, based on the weight of said oligomer.*

*42. The dispensing elastomeric film of claim 39 further comprising a coating of a pressure sensitive adhesive on one surface of said film.*

*43. The dispensing elastomeric film of claim 39 wherein a photoinitiator is admixed with said oligomer.*

*44. The dispensing elastomeric film of claim 43 wherein said photoinitiator is selected from the group consisting of diacetoxyacetobenzophenone, benzophenone, diethoxyacetophenone 4-morpholine benzophenone, aminobenzophenone and 4'-methoxyacetophenone.*

*45. The dispensing elastomeric film of claim 39 wherein said film further comprises at least one non-reactive thixotropic agent.*

*46. The dispensing elastomeric film of claim 45 wherein said non-reactive thixotropic agent is selected from the group consisting of pyrogenic silica and bentonite clays.*

*47. The dispensing elastomeric film of claim 39 wherein the vinyl terminator oligomer is co-dissolved with a polyurethane polymer which is the reaction product of:*

*(d) dicyclohexyl methane diisocyanate;*

*(e) a polytetramethylene ether polyol having a number average molecular weight in the range of 1000–3000 Daltons; and*

*(f) 1,4-butane diol;*

*and the resulting solution is formed into said film.*

*48. The dispensing elastomeric film of claim 47 wherein said film contains 80–99 parts by weight of said vinyl terminated oligomer and 1–20 parts by weight of said polyurethane polymer.*

*49. The dispensing elastomeric film of claim 47 further comprising a textile fabric, said film being formed on said textile fabric.*

*50. The dispensing elastomeric film of claim 49 wherein said textile fabric is first coated with a polyurethane polymer that is the reaction product of:*

*dicyclohexyl methane diisocyanate;*

*a polytetramethylene ether polyol having a number average molecular weight in the range of 1000–3000 Daltons; and*

*1,4-butane diol*

*and then coated with said solvent solution.*

*51. The dispensing elastomeric film of claim 50 further comprising a coating of a pressure sensitive adhesive on one surface of said film.*

*52. The dispensing elastomeric film of claim 47 wherein said film further comprises at least one non-reactive thixotropic agent.*

*53. The dispensing elastomeric film of claim 52 wherein said non-reactive thixotropic agent is selected from the group consisting of pyrogenic silica and bentonite clays.*

*54. A process for forming and dispensing elastomeric film comprising:*

*(1) preparing a reaction product consisting essentially of isophorone diisocyanate, a macroglycol and a monomer containing hydroxyl and vinyl groups by reacting (a) isophorone diisocyanate and (b) a macroglycol in the presence of a catalyst to form an isocyanate terminated prepolymer and reacting said prepolymer with (c) a monomer containing hydroxyl and vinyl groups to form an ultraviolet-curable, vinyl terminated polyurethane liquid oligomer;*

*(2) admixing said vinyl terminated oligomer with an agent to be dispensed to form an UV-curable mixture;*

*(3) forming the UV-curable mixture into a film; and*

*(4) curing said film by exposure to ultraviolet light.*

*55. The process of claim 54 wherein a photoinitiator is admixed with said oligomer and wherein said curing is at approximately room temperature.*

*56. The process of claim 54 wherein said macroglycol is polypropylene glycol having a number average molecular weight of 500–5000 daltons and said monomer is hydroxyethyl methacrylate.*

*57. The process of claim 54 wherein said agent is added in an amount 1–10% by weight, based on the weight of said oligomer.*

*58. The process of claim 54 further comprising coating one surface of said film with a pressure sensitive adhesive.*

*59. The process of claim 55 wherein said photoinitiator is selected from the group consisting of diacetoxyacetobenzophenone, benzophenone, 4-aminobenzophenone and 4'-methoxyacetophenone.*

*60. The process of claim 55 further comprising mixing said oligomer with at least one non-reactive thixotropic agent.*

*61. The process of claim 60 wherein said non-reactive thixotropic agent is selected from the group consisting of pyrogenic silica and bentonite clays.*

*62. A process in accordance with claim 54 wherein said vinyl terminated oligomer is dissolved in an organic solvent and the agent is admixed in said solvent solution.*

*63. A process in accordance with claim 62 wherein the vinyl terminated oligomer is co-dissolved with a polyurethane polymer which is the reaction product of:*

*(d) dicyclohexyl methane diisocyanate;*

*(e) a polytetramethylene ether polyol having a number average molecular weight in the range of 1000–3000 daltons; and*

*(f) 1,4-butane diol.*

*64. The process of claim 63 wherein 80–99 parts by weight of said vinyl terminated oligomer are co-dissolved with 1–20 parts by weight of siad polyurethane polymer.*

*65. The process of claim 63 wherein said monomer is hydroxyethyl methacrylate and said macroglycol is a polypropylene glycol having a number average molecular weight of 500–3000 daltons.*

*66. The process of claim 63 further comprising providing a textile fabric and coating said textile fabric with said solvent solution to form said film.*

*67. The process of claim 66 wherein said textile fabric is first coated with a polyurethane polymer that is the reaction product of:*

*dicyclohexyl methane diisocyanate;*

*a polytetramethylene ether polyol having a number average molecular weight in the range of 1000–3000 daltons; and*

*1,4-butane diol*

*and then coated with said solvent solution.*

*68. A process in accordance with claim 54 wherein a sufficient amount of (c) is added so that only compounds with number average molecular weights of 1500–5000 are present.*

* * * * *